(12) United States Patent  
Kleine-Kleffmann et al.

(10) Patent No.: US 9,663,410 B2
(45) Date of Patent: May 30, 2017

(54) COMPOSITION OF A MAGNESIUM SULFATE/UREA COMPOUND

(71) Applicant: K+S KALI GmbH, Kassel (DE)

(72) Inventors: Ulrich Kleine-Kleffmann, Bad Hersfeld (DE); Wolfgang Walczyk, Heringen (DE)

(73) Assignee: K+S Kali GmbH, Kassel (DE)

( * ) Notice: Subject to any disclaimer, the term of this patent is extended or adjusted under 35 U.S.C. 154(b) by 0 days.

(21) Appl. No.: 14/369,961

(22) PCT Filed: Dec. 28, 2012

(86) PCT No.: PCT/EP2012/077017
§ 371 (c)(1),
(2) Date: Jun. 30, 2014

(87) PCT Pub. No.: WO2013/098367
PCT Pub. Date: Jul. 4, 2013

(65) Prior Publication Data
US 2014/0360239 A1 Dec. 11, 2014

(30) Foreign Application Priority Data
Dec. 30, 2011 (EP) .................................. 11196218

(51) Int. Cl.
C05C 9/00 (2006.01)
C07C 273/02 (2006.01)
C05D 9/00 (2006.01)

(52) U.S. Cl.
CPC .................. *C05C 9/00* (2013.01); *C05D 9/00* (2013.01); *C07C 273/02* (2013.01)

(58) Field of Classification Search
None
See application file for complete search history.

(56) References Cited

U.S. PATENT DOCUMENTS 5,431,708 A 7/1995 Lehmann et al.
2010/0218575 A1* 9/2010 Wissemeier et al. ............. 71/28

FOREIGN PATENT DOCUMENTS

DE 42 32 567 C1 2/1994
GB 1 359 884 7/1974

OTHER PUBLICATIONS

Sulaimankulov, K. et al, "Reactions of urea with sulfates of bivalent metal. I. The isotherms of the system water-urea-magnesium sulfate at 0, 30, and 45" Zhurnal Neorganicheskoi Khimii (1957), 2, 2668-75.*

(Continued)

*Primary Examiner* — Wayne Langel
(74) *Attorney, Agent, or Firm* — Oblon, McClelland, Maier & Neustadt, L.L.P.

(57) ABSTRACT

The subject of the invention is a composition containing at least 80 wt. %, with reference to the total weight of the composition, of a magnesium-sulfate-urea compound of Formula (I):

$$[MgSO_4 \cdot m\ CO(NH_2)_2 \cdot n\ H_2O] \qquad (I),$$

in which m is in the range from 0.9 to 1.1 and n is in the range from 2.1 to 3.1, where the composition, with reference to the total weight of the composition, contains less than 10 wt. % free $MgSO_4$ in the form of the anhydrate or in the form of urea-free hydrates of the magnesium sulfate, such as magnesium sulfate or magnesium-sulfate hexahydrate and/or less than 10 wt. % uncombined urea. In particular, m in Formula (I) indicates the value 1. In particular, n in Formula (I) indicates the value 3.
The invention also concerns the manufacture of the compositions and their utilization as fertilizers or fertilizer additives.

16 Claims, 1 Drawing Sheet

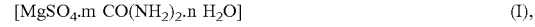

(56) References Cited

OTHER PUBLICATIONS

Zhang, Fengxing et al, "Study on the isothermal solubility of $MgSO_4$—$Co(NH_2)_2$—$H_2O$ ternary system at 25 C" Wuji Huaxue Xuebao (1997), 13(4), 375-379 (Abstract only).*
International Search Report issued Apr. 8, 2013 in corresponding PCT/EP2012/077017.
G.P. Shkrobot, et al., "Magnesium sulfate-cobalt sulfate-urea-water system at 20.degree. C", XP-002678411, Zhurnal Neorganicheskoi Khimii (1976), 21(5), Journal, 1 p. (derwent abstract only).
Colin W. Whittaker, et al., "The System Magnesium Sulfate-Urea-Water at 30° C.", Journal of American Society, vol. 58, Oct. 1, 1936, XP-002678412, pp. 1975-1977.
W Von Rheinbaben, "Effect of magnesium sulphate addition to urea on nitrogen loss due to ammonia volatilization", Fertilizer Research vol. 11, No. 2, XP008152705, Jan. 1, 1987, pp. 149-159.

* cited by examiner

K + S Kali GmbH

Specifications in Angstrom (1 Å = 0.1 nM)

| Urea CO(NH₂)₂ | |
|---|---|
| d-value (Å) | Intensity (%) |
| 3.9916 | 100 |
| 3.6138 | 24 |
| 3.0435 | 25 |
| 2.8225 | 7 |
| 2.5245 | 11 |
| 2.4203 | 9 |
| 2.1711 | 5 |

| Magnesium sulfate MgSO₄·7H₂O | |
|---|---|
| d-value (Å) | Intensity (%) |
| 5.9800 | 30 |
| 5.9400 | 16 |
| 5.3400 | 30 |
| 5.3100 | 20 |
| 4.5090 | 6 |
| 4.4770 | 12 |
| 4.2160 | 100 |
| 4.2000 | 75 |
| 3.7820 | 12 |
| 3.7570 | 7 |
| 3.4490 | 10 |
| 3.4250 | 10 |
| 2.9970 | 7 |
| 2.9830 | 12 |
| 2.9740 | 12 |
| 2.8800 | 20 |
| 2.7440 | 18 |
| 2.7220 | 2 |
| 2.6740 | 20 |
| 2.6580 | 25 |
| 2.3820 | 7 |
| 2.2550 | 6 |
| 2.2040 | 10 |
| 2.1320 | 6 |
| 2.1080 | 10 |
| 2.1000 | 5 |
| 1.9593 | 7 |
| 1.9550 | 5 |
| 1.8930 | 6 |
| 1.6348 | 5 |

| Gravel MgSO₄·H₂O | |
|---|---|
| d-value (Å) | Intensity (%) |
| 4.8150 | 75 |
| 3.4050 | 100 |
| 3.3510 | 70 |
| 3.3130 | 70 |
| 3.1060 | 13 |
| 3.0510 | 40 |
| 2.5600 | 35 |
| 2.5230 | 30 |
| 2.1850 | 7 |
| 2.0990 | 9 |
| 2.0540 | 20 |
| 1.9650 | 8 |
| 1.9039 | 5 |
| 1.9039 | 5 |
| 1.6750 | 14 |
| 1.6577 | 5 |
| 1.6227 | 8 |
| 1.5866 | 7 |

| CMS MgSO₄ | |
|---|---|
| d-value (Å) | Intensity (%) |
| 4.1500 | 30 |
| 3.8700 | 10 |
| 3.6100 | 70 |
| 3.5300 | 100 |
| 3.3500 | 18 |
| 3.1800 | 16 |
| 2.6390 | 25 |
| 2.6050 | 16 |
| 2.4480 | 18 |
| 2.3710 | 10 |
| 2.3050 | 16 |
| 2.2860 | 12 |
| 2.1630 | 6 |
| 2.0420 | 8 |
| 2.0180 | 6 |
| 1.9650 | 8 |
| 1.8050 | 8 |
| 1.7630 | 16 |
| 1.6730 | 10 |

| Magnesium sulfate urea MgSO₄·CO(NH₂)₂·3H₂O | |
|---|---|
| d-value (Å) | Intensity |
| 10.1656 | 100 |
| 6.1384 | 7 |
| 5.0928 | 8 |
| 4.8050 | 9 |
| 4.2520 | 13 |
| 4.0752 | 21 |
| 3.8527 | 39 |
| 3.5177 | 7 |
| 3.3994 | 63 |
| 3.2015 | 9 |
| 3.0064 | 13 |
| 2.9572 | 6 |
| 2.9318 | 15 |
| 2.7558 | 15 |
| 2.5505 | 7 |
| 2.4920 | 8 |
| 2.4767 | 5 |
| 2.2944 | 6 |
| 2.2649 | 6 |
| 2.2609 | 8 |
| 2.1393 | 6 |
| 2.1293 | 6 | ns
COMPOSITION OF A MAGNESIUM SULFATE/UREA COMPOUND

CROSS REFERENCE TO RELATED APPLICATIONS

The present application is a 35 U.S.C. § 371 national stage patent application of International patent application PCT/EP2012/077017, filed on Dec. 28, 2012, published as WO/2013/098367 on Jul. 4, 2013, the text of which is incorporated by reference, and claims the benefit of the filing date of European application no.11196218.9, filed on Dec. 30, 2011, the text of which is also incorporated by reference.

BACKGROUND OF THE INVENTION

Field of the Invention

The existing invention concerns compositions of a magnesium-sulfate-urea compound of Formula I

where m is in the range of 0.9 to 1.1 and n is in the range of 2.9 to 3.1, the manufacture of the compositions and their utilization as fertilizers or fertilizer additives.

DISCUSSION OF THE BACKGROUND

Although magnesium exists as the eighth most frequent element in the crust of the earth at approx. 1.94%, soils often indicate a defect in magnesium. Therefore, magnesium salts find wide utilization as fertilizers or fertilizer additives. In particular, salts of magnesium are employed as fertilizers or fertilizer additives. Usually these salts are employed as magnesium sulfate in combination with macro-nutrients, such as potassium, phosphorus or nitrogen, as well as with trace elements, such as manganese, zinc, copper, iron, cobalt, molybdenum or boron.

Essentially, it is of interest to provide as many macro and micro-nutrients as possible together in a fertilizer composition. However, limits are set on the joint employment of magnesium and nitrogen. A simple solid-matter mixture of magnesium sulfate ($MgSO_4 7H_2O$) and urea is not storage-stable. Even after a short time a reaction of the two mixture partners occurs, in this event pasty masses are formed which, due to their high hygroscopicity, liquefy easily and furthermore easily deliquesce and are therefore hard to handle and cannot be worked into solid fertilizer compositions in particular.

Magnesium-sulfate-urea compounds of Formula I are, on principle, known from the literature. Thus Colin et al, in the *Journal of American Society,* 1936, 58. 1975 describes the manufacture of magnesium-sulfate-urea complexes, where the relationship of magnesium sulfate to urea is 1 to 1. Equimolar quantities of magnesium sulfate are mixed with urea for the manufacture of this compound ($MgSO_4.7H_2O$). In this case, a crystalline product is deposited.

Our own investigations have indicated that this case does not involve the pure product, rather a mixture from the compound of Formula I with magnesium sulfate ($MgSO_4.7H_2O$) and non-bonded urea. A further cleaning off of the product is not possible.

T. Hitomi et al. *Nippon Dojo Hiryogaku Zosshi,* 1965, 36(3), 63 report about investigations regarding the hygroscopicity of artificial fertilizers. These reports indicated that the magnesium-sulfate-urea compound $MgSO_4.5$-$6CO(NH_2)_2.2H_2O$ is exceptionally hygroscopic. Therefore, it is not possible to employ these compounds in solid fertilizers.

SUMMARY OF THE INVENTION

Therefore, the basic task taken as a basis for the invention is to provide a non-liquefying composition of magnesium-sulfate urea, which eliminates the above-designated disadvantages of the magnesium-sulfur-nitrogen compounds, in accordance with the state of the art technology.

Surprisingly, it has been found that, by means of suitable processes, the magnesium-sulfate-urea compound of Formula I can be manufactured in a quick and simple manner, in very good yields, as a pure, crystalline and storage-stable composition which does not indicate the disadvantages of the state of the art technology and which is not particularly hygroscopic. The composition thus obtained can therefore be worked in especially well with fertilizer compositions.

BRIEF DESCRIPTION OF THE DRAWING

The FIGURE shows a list of the characteristic reflexes (indicated as d-values in Angstroms) and their relative intensity in the X-ray powder diffractogram of urea (CO$(NH_2)_2$, magnesium sulfate ($MgSO_4$ * $7H_2O$), kieserite ($MgSO_4 H_2O$), anhydrous magnesium sulfate ($MgSO_4$) and the compound of Formula I ($MgSO_4 CO(NH_2)_2$ ' $3 H_2O$).

DETAILED DESCRIPTION OF THE INVENTION

The subject of the invention is a composition, containing at least 80 wt. %, with reference to the total weight of the composition of a magnesium-sulfate-urea compound of Formula (I):

where m is in the range 0.9 to 1.1 and n is in the range 2.1 to 3.1, where the composition, with reference to the total weight of the composition, contains less than 10 wt. % free $MgSO_4$ in the form of the anhydrate, or in the form of urea-free hydrates of the magnesium sulfate, such as magnesium sulfate or magnesium-sulfate hexahydrate and/or less than 10 wt. % uncombined urea. In particular, m in Formula (I) indicates the value 1. In particular n in Formula (I) indicates the value 3.

The compositions, with regard to the invention, are solid, generally crystalline compositions which are not hygroscopic or are only slightly hygroscopic. They indicate only a small content of starting materials, different to the state of the art compositions of the compound of Formula I the state of the art. Furthermore, the compound in them is accessible in very good yields and available in storage-stable form. In addition, these compositions can be manufactured easily in powder form or in the form of granulates, and therefore employed as fertilizers in a simple manner or inserted in conventional fertilizer compositions. Furthermore, solutions of the compositions can be manufactured by dissolving the compositions in a solvent, for example water.

Preferably, the composition includes less than 5 wt. % free $MgSO_4$ in the form of the anhydrate or in the form of urea-free hydrates of the magnesium sulfate, or less than 5 wt. % uncombined urea, in each case with reference to the total weight of the composition. In particular, the composition includes less than 5 wt. %, especially less than 3 wt. %, of free $MgSO_4$ in the form of the anhydrate or in the form of urea-free hydrates of the magnesium sulfate, and simultaneously less than 5 wt. %, in particular less than 3 wt. %, of uncombined urea, in each case with reference to the total weight of the composition.

The content of free $MgSO_4$ in the form of the anhydrate or in the form of hydrates of the magnesium sulfate, such as magnesium sulfate, magnesium-sulfate monohydrate or magnesium-sulfate hexahydrate, as well as the content of free urea, can be determined by means of X-ray powder diffractometry. This is achieved through comparison of a powder diffractogram with reference powder diffractograms of the contamination, such as $MgSO_4$ in the form of the anhydrate, magnesium sulfate or also magnesium-sulfate hexahydrate and urea. Such methods are known in the specialist trade and can be implemented in a known manner. For example, this can be achieved with the aid of the powder X-ray diffractometry software: "EVA" Ver. 12.0.0.0 of the Co. Bruker AXS, database: File Powder Diffraction (PDF-2, Release 1999; Data sets 1-49, plus 70-86) of the International Center for Diffraction Data (ICDD).

From the absence of the reflexes characteristic for the contamination, it can furthermore be concluded that the content of the respective contamination, in accordance with qualitative evaluation of the diagram RDA, is vanishingly small. The characteristic reflexes for $MgSO_4$ in the form of the anhydrate, magnesium sulfate, magnesium-sulfate hexahydrate, as well as urea, can be taken from the literature or relevant databases, such as those of the International Center for Diffraction Data (JCPDS).

The compound of Formula I included in the compositions used in the invention indicates, in an X-ray powder diffractogram recorded at 25° C. (Cu—Kα radiation: λ=1.5413 A), at least 3 and in particular at least 5, and especially at least 7 or all d-values of the following Table 1, where it indicates preferably at least 3, in particular at least 5 and especially at least 7 of the respective reflexes, whose relative intensity is greater than 8%, with reference to the intensity of the strongest peak (100% rel. intensity).

Table 1 indicates the characteristic reflexes of the Compound I as network-designation separation distances d (in Angstroms), which can be calculated from the Bragg relationship 2Θ-values.

TABLE 1

| d-value (A) | rel. intensity (%) |
| --- | --- |
| 10.1656 | 100 |
| 3.3994 | 63 |
| 3.8527 | 39 |
| 4.0752 | 21 |
| 2.9318 | 15 |
| 2.7558 | 15 |
| 4.2520 | 13 |
| 3.0064 | 13 |
| 4.8050 | 9 |
| 3.2015 | 9 |
| 5.0928 | 8 |
| 2.2609 | 8 |
| 2.4920 | 8 |
| 6.1384 | 7 |
| 3.5177 | 7 |
| 2.5505 | 7 |
| 2.2649 | 6 |
| 2.9572 | 6 |
| 2.2944 | 6 |
| 2.1393 | 6 |
| 2.1293 | 6 |
| 2.4767 | 5 |

The compositions included in those in the invention can be identified in an X-ray powder diffractogram of the composition recorded at 25° C. (Cu—Kα radiation: λ=1.5413), by means of the reflexes indicated in the following Table 2, where for the identification typically at least 3 and in particular at least 5 of the indicated d-values are referred to with a relative intensity greater than 10%. A complete listing of the d-values is represented in Illustration 1.

TABLE 2

| Contamination | d-value (A) | rel. intensity (%) |
| --- | --- | --- |
| Urea | 3.9916 | 100 |
|  | 3.6138 | 24 |
|  | 3.0435 | 25 |
| $MgSO_4 \cdot 7H_2O$ | 4.2160 | 100 |
|  | 4.2000 | 75 |
|  | 5.3400 | 30 |
|  | 5.9800 | 30 |
| $MgSO_4 \cdot H_2O$ | 3.4050 | 100 |
|  | 4.8150 | 75 |
|  | 3.3510 | 70 |
|  | 3.3130 | 70 |
| $MgSO_4$ | 3.5300 | 100 |
|  | 3.6100 | 70 |
|  | 4.1500 | 30 |

The stoichiometry of the compound can be determined by elemental analysis, considering the existing contamination.

A process for the manufacture of the compositions, with regard to the invention, of the magnesium-sulfate-urea compound of Formula (I) has further been found, which is characterized in that anhydrous magnesium sulfate is transformed with urea and water. This process is also designated as Process 1 in the following.

Preferably, in Process I, anhydrous magnesium sulfate, urea and water are used in the stoichiometry necessary for the compound, i.e. in a mol ratio of magnesium sulfate to urea in the range from 1:0.9 to 1:1.1, in particular 1:0.95 to 1:1.05 and especially 1:0.98 to 1:1.02, and a ratio of magnesium sulfate to water in the range from 1:2.9 to 1:3.1, in particular 1:2.95 to 1:3.05 and especially 1:2.98 to 1:3.02.

In particular, for the conversion in accordance with Process 1, anhydrous magnesium sulfate is mixed with urea in the above-designated mol ratio, and water is added to that in the above-designated mol ratio. A possible structuring of Process 1 is described in Example 1.

The conversion in accordance with Process 1 is exothermic. In this case, it has proved useful to carry out the conversion of the co-reactants of anhydrous magnesium sulfate, urea and water in Process 1 through utilization of the heat of reaction. Preferably, a temperature of 70° C. is not exceeded in this case. Where appropriate, the reaction mixture is therefore cooled. In particular, the conversion is implemented with temperatures in the range from 30 to 70° C. Possible measures are taken to route back into the reaction any water which evaporates during the conversion. Preferably, during the conversion, the generally liquid or plastic reaction mixture is intermixed, for example with suitable agitation or kneading equipment, or by means of extruder.

On completion of the reaction, the composition formed is generally allowed to cool down to ambient temperature. In this case, a solid mass is typically obtained which can be comminuted in a manner known.

In accordance with a preferred implementation form of Process 1, the liquid or plastic reaction mixture, during the conversion or immediately after the conversion when the reaction masses is still plastic, is target modified into a required particle size and shape, e.g. through granulation or comminution. The granulating can be implemented in the usual manner, e.g. where the conversion is implemented in a mixer or rolling drum or granulation plate. Usually the granulation or comminution is carried out in such a manner that a maximum of 10 wt. % of the particles indicate a diameter above 5 mm in the granulate obtained. Preferably, the granulating is carried out so that at least 90 wt. % of the particles indicate a particle diameter in the range from 0.5 to 5 mm. The particle diameter can be determined by sieve analysis.

However, it is also possible to comminute the solid composition obtained after the cooling down of the reaction mixture. Usual equipment for the comminution can be employed for the comminution of the composition of solid matter, preferably impact or rebound crusher mills, among other things also jaw crushers, rotating crushers, roll crushers, hammer crushers, thumb crushers, worm-drive crushers, roller grinding mills, impact and centrifuging mills. Usually, the comminution is to be carried out until at least 90 wt. % of the particles indicate a diameter less than 5 mm. Preferably the comminution is be carried out so that at least 90 wt. % of the particles indicate a particle diameter in the range from 0.5 to 5 mm. The particle diameter can be determined by sieve analysis.

Process 1 and Process 3, with regard to the invention, described below, enable the manufacture of the compound of Formula I in high yield, generally virtually 100%, with reference to magnesium sulfate and urea. The content of free magnesium sulfate, whether it is obtained in the form of the anhydrate or a urea-free hydrate, is less than 10 wt. % and in particular less than 5 wt. %. Furthermore, the invention-related process enables the manufacture of compositions of the compound of Formula I which contain less than 10 wt. %, and in particular less than 5 wt. %, of uncombined urea.

Different to the process of the state of the art of the technology, Processes 1 and 3, in regard to the invention, do not require any filtration and drying steps and are therefore particularly simple and feasible with high energy efficiency.

As well as the above-described Process 1, Process 2 for the manufacture of magnesium-sulfate-urea compounds of Formula (I) has been found, which is characterized in that, at first a magnesium sulfate mixture (MgSO$_4$.7H$_2$O) with urea in the mol ratio magnesium sulfate is converted to urea in the range from 1:0.9 to 1:1.1, in particular 1:0.95 to 1:1.05 and especially 1:0.98 to 1:1.02, and further urea is added to the mixture obtained during conversion. This process is designated as Process 2 in the following. A possible structuring of Process 2 is described in Example 2.

Preferably, in case of the conversion in accordance with Process 2, more urea in a quantity from 10 to 30 mol %, with reference to the urea quantity initially used, is added to the mixture of magnesium sulfate (MgSO$_4$.7H$_2$O) and urea. The addition can be implemented in one portion or in several portions, or also continuously.

The addition of the further urea is generally implemented at the time when the magnesium sulfate (MgSO$_4$.7H$_2$O) and urea are already mixed with each other.

Preferably, the conversion is implemented, in accordance with Process 2, with temperatures in the range from 20 to 70° C., and in particular in the range from 40 to 60° C. Since the conversion in accordance with Process 2 scarcely indicates any heat of reaction, the mixture of magnesium sulfate and urea is possible when warmed up to the required temperature.

Preferably during conversion, the generally liquid or plastic reaction mixture is intermixed, for example with suitable agitation or kneading equipment.

Different to Process 1, the reaction mixture obtained in Process 2 results in the form of a diluted suspension. From this, the composition, with regard to the invention, can be isolated by usual methods of the separation of solid and liquid phases, for example through filtration or centrifuging. Generally, a drying step will follow. Preferably the drying is implemented with temperatures in the range from 30 to 70° C., and in particular in the range from 30 to 50° C.

The composition, obtained via the invention, according to Process 2, results typically in a fine-particle form in which less than 90 wt. % of the particles indicate a diameter above 1 mm. Preferably, at least 90 wt. % of the particles indicate a particle diameter less than 2 mm. The particle diameter can be determined by sieve analysis.

Process 2, with regard to the invention, also enables the manufacture of the compound of Formula I in high yield, generally at least 70%, with reference to magnesium sulfate. The content of free magnesium sulfate, whether it is obtained in the form of the anhydrate or a urea-free hydrate, is less than 10 wt. %, and in particular less than 5 wt. %. Furthermore, the invention-related process enables the manufacture of compositions of the compound of Formula I, which contain less than 10 wt. % and in particular less than 5 wt. % of uncombined urea.

As well as the above described Processes 1 and 2, a further Process 3 was found for the manufacture of magnesium-sulfate-urea compounds of Formula (I), which is characterized in that a mixture of anhydrous magnesium sulfate, urea and magnesium sulfate (Mg SO$_4$*7H$_2$O) is at first converted.

A possible structuring of Process 3 is described in Example 3.

Preferably, in case of the conversion in accordance with Process 2, anhydrous magnesium sulfate, urea and magnesium sulfate are used in the stoichiometry necessary for the compound, i.e. in a mol ratio of anhydrous magnesium sulfate:urea in the range from 1:1.65 to 1:1.85 and in the mol ratio anhydrous magnesium sulfate:magnesium sulfate in the range from 1:0.65 to 1:0.85, where the mol ratio of urea to the total amount at anhydrous magnesium sulfate and magnesium sulfate lies in the range from 0.9:1 to 1.1:1. This process is designated as Process 3 in the following.

Preferably, the mixture of the above-designated starting materials is heated to 30 to 60° C. first of all, preferably to 50° C. Preferably, the generally liquid or plastic reaction mixture is intermixed during conversion, for example by means of suitable agitation or kneading equipment or extruder. The arising pasty mass of the composition formed solidifies after cooling to ambient temperature. In this case, a solid mass is obtained which can be comminuted in a known manner.

In accordance with the preferred implementation form of Process 3, the liquid or plastic reaction mixture, during the conversion or immediately after the conversion, when the reaction masses is still plastic, is target-modified into the required particle size and shape, e.g. through granulation or comminution. The granulating can be implemented in the usual manner, e.g. where the conversion is implemented in a mixer or rolling drum or granulation plate. Usually, the granulation or comminution is carried out in such a manner that a maximum of 10 wt. % of the particles indicate a diameter above 5 mm in the granulate obtained. Preferably, the granulating is carried out so that at least 90 wt. % of the particles indicate a particle diameter in the range from 0.5 to 5 mm. The particle diameter can be determined by sieve analysis.

However, it is also possible to comminute the solid composition obtained after the cooling down of the reaction mixture. Usual equipment for the comminution can be employed for the comminution of the composition of solid matter, preferably impact or rebound crusher mills, among other things also jaw crushers, rotating crushers, roll crushers, hammer crushers, thumb crushers, worm-drive crushers, roller grinding mills, impact and centrifuging mills.

Usually, the comminution is to be carried out until at least 90 wt. % of the particles indicate a diameter less than 5 mm. Preferably, the comminution is be carried out so that at least 90 wt. % of the particles indicate a particle diameter in the range from 0.5 to 5 mm. The particle diameter can be determined by sieve analysis.

Different than in the process of the state of the art of the technology, the invention-related Process 3 does not require any filtration and drying steps and is therefore particularly simple and feasible with high energy efficiency. In addition, no additional water has to be added into the reaction mixture with Process 3.

The invention further concerns the utilization of the compositions, with regard to the invention, of Formula (I) as fertilizers or as a fertilizer additives.

The composition, with regard to the invention, is as such suitable as fertilizer and represents the invention-related composition fertilizer composition of nitrogen-magnesium-sulfur. However, it is also suitable as a nitrogen supplier, in particular for conventional magnesium sulfur fertilizer compositions. As a result of the addition of conventional magnesium sulfur fertilizer compositions, nitrogen-magnesium-sulfur fertilizer compositions can thus be provided in a simple manner.

Such nitrogen-magnesium-sulfur fertilizer compositions include the compound of Formula I typically in a quantity from 1 to 100 wt. %.

As well as the compound of Formula I and magnesium sulfate, preferably in the form of magnesium sulfate, the nitrogen-magnesium-sulfur fertilizer compositions can possibly contain further macro-nutrients, such as phosphorus, preferably in the form of phosphates, and/or potassium, as well as micro-nutrients such as manganese, zinc, copper, iron, cobalt, molybdenum and boron. Manganese and zinc are employed in this case, preferably in the form of their sulfates. Copper, cobalt and iron are employed preferably in the form of chelates, e.g. with EDTA. Boron is employed preferably as sodium borate or boric acid. Molybdenum is employed preferably as sodium molybdate or ammonium molybdate, or as a mixture of these.

Preferably, the composition is employed as an additive in fertilizers including magnesium sulfate. Such fertilizers and/or fertilizer compositions are new and are also the subject of the invention.

In particular, as well as magnesium sulfate, the fertilizer composition, with regard to the invention, includes 90 wt. %, in particular 5 to 50 wt. % and especially 10 to 30 wt. %, with reference to the total weight of the fertilizer composition, of the compound of Formula I, as well as possibly one or more of the above-designated micro-nutrients. The content of the micro-nutrients, calculated as an element, is generally not more than 30 wt. %, with reference to the total weight of the fertilizer composition and is frequently in the range from 0.1 to 10 wt. %, provided this is desired.

The composition, with regard to the invention, of the compound of Formula I can also be employed together with so-called nitrification inhibitors and/or urease inhibitors. In this case, the composition, with regard to the invention, of the compound of Formula I can be employed either in the mixture with nitrification inhibitors or in the mixture with urease inhibitors or in the mixture of nitrification inhibitors and urease inhibitors.

Fertilizer compositions, as well as including at least one compound of Formula I in the form of the invention-related composition and at least a further component part which is selected under urease inhibitors and nitrification inhibitors, are also the subject of the existing invention.

Suitable urease inhibitors are known to the specialist trade, for example from Kiss et al. (Kiss, S, Simihaeian, M. 2002, *Improving Efficiency of Urea Fertilizers by Inhibition of Soil Urease Activity*, ISBN 1-4020-0493-1, Kluwer Academic Publishers, Dordrecht, The Netherlands). Suitable urease inhibitors are, in particular, N-alkyl phosphoric acid amide and alkylthiophosphoric acid triamide and their mixtures, as they are known e.g. from WO 2009/079994 and the literature quoted there. N-n-butylthio phosphoric acid triamide (NBPT), N-n-propyltbio phosphoric acid triamide (NPPT) and their mixtures are preferred.

Suitable nitrification inhibitors, as well as di-cyanogen diamide, are particularly pyrazoles and their acid additive salts, in particular their phosphoric acid additive salts, as well as 1-carboxyalkylpyrazole and their mixtures. In this case, the pyrazoles and 1-carboxyalkylpyrazole on the carbon atoms can be substituted through one or more e.g. 1 or 2 substituents from the Ci C4 alkyl group, in particular methyl, nitro and halogen, in particular chlorine. Such compounds and their utilization as nitrification inhibitors are known for example from U.S. Pat. No. 3,635,690, U.S. Pat. No. 4,969,946, EP 0808298 and EP 1120388.

The preferred nitrification inhibitors are 3-methyl-pyrazole compounds, such as 4-chlor-3-methylpyrazol and its acid additive salts, N-hydroxymethyl-4-chloro-3-methyl-pyrazole and its acid additive salts, as well as 3.4-dimethyl pyrazole (DMP) compounds, such as 2-(3.4-dimethylpyrazole-1-yl)-succinic acid, N-hydroxymethyl 3.4-dimethyl-pyrazole and its acid additive salts, as well as particularly 3.4-dimethyl pyrazole and the acid additive salts of 3.4-dimethylpyrazole, especially its phosphoric acid additive salts (DMPP).

Such fertilizer compositions include the compound of Formula I and at least one further component part from the group of the nitrification inhibitors and urease inhibitors, generally in a quantity from 0.001 to 5 wt. %, in particular in a quantity from 0.002 to 3 wt. %, with reference to the total weight of the fertilizer composition.

Provided that such fertilizer compositions include at least one urease inhibitor, the concentration of urease inhibitors is generally 0.001 to 3 wt. %, in particular 0.002 to 2 wt. %, with reference to the urea in the fertilizer composition.

Provided that such fertilizer compositions include at least one nitrification inhibitor, the concentration of nitrification inhibitors is generally 0.01 to 3 wt. %, in particular 0.02 to 2 wt. %, with reference to the total weight of the fertilizer composition, in the case of acid additive salts of pyrazole compounds, calculated as salt.

Provided that such fertilizer compositions include at least one urease inhibitor and at least one nitrification inhibitor, the total concentration of urease inhibitors+nitrification inhibitors is generally 0.011 to 5 wt. %, in particular 0.022 to 3 wt. %, with reference to the total weight of the fertilizer composition. Typically, the weight ratio of at least one nitrification inhibitor to at least one urease inhibitor is generally 1:10 to 10:1 and preferably 1:5 to 5:1.

Fertilizer compositions which also include at least one a compound of Formula I in the form of the composition, with regard to the invention, and at least one further component part, which is selected under urease inhibitors and nitrification inhibitors, can possibly additionally include magnesium, preferably in the form of magnesium sulfate, and/or further macro-nutrients such as phosphorus, preferably in the form of phosphates, and/or potassium, as well as micronutrients such as manganese, zinc, copper, iron, cobalt, molybdenum and/or boron.

Manganese and zinc are preferably employed in the form of their sulfates in this case. Copper, cobalt and iron are employed preferably in the form of chelates, e.g. with EDTA. Boron is employed preferably as sodium borate or boric acid. Molybdenum is employed preferably as sodium or ammonium molybdate, or as a mixture of these. With regard to the quantity parts of the compound of Formula I and the micro-nutrients, the above statement applies.

As already mentioned above, solutions of the compositions, in regard to the invention, can be manufactured by dissolving those compositions in a solvent, for example water. In this way, the compositions, with regard to the invention, can be employed (among other things) for irrigation fertilizing (fertigation) in liquid fertilizers. Water, which cannot be taken up by the roots of the plant cultures, since e.g. the underground or seeped-through soil layers cannot be reached by roots, is designated as surplus water. The implementation of artificial irrigation fertilizing with liquid fertilizing of the invention-related composition can be implemented so that essentially no surplus water results. The irrigation fertilizing is preferred with liquid fertilizer of the composition, in relation to the invention, in particular a mixture from liquid fertilizer of the said composition with further additives, e.g. urease inhibitor, is carried out so that no surplus water results.

The composition, with regard to the invention and the invention-related processes are explained in more detail through the following examples and Illustration 1.

The recording of the X-ray powder diffractograms is implemented with a Type D 8 Advance Diffractometer of the Co. Bruker, AXS (298 K, Cu—Kα radiation: λ=1.5413 A), increment: 0.018385738, signal element: 0.2 seconds, detector: Lynx Eye.

The elemental analyses are implemented by:
N-Best. DIN ISO 13878, TOC-Best., DIN EN 1484, Mg/S association method LUFA (K+S 0905.01)

Example 1

256.5 g magnesium sulfate anhydrous and 128 g granulated urea were mixed well in an agitation container. Then under constant intensive agitation, 115.5 g water was added. At first, a fluid porridge was formed and the mixture warmed up to 52° C. With further agitation time, the mixture became increasingly more solid, lumps were formed which were crushed again and again. After 10 hours, the mass was compacted and after 24 hours it was very hard. After a further 24 hours rest, the mass was comminuted with a hammer to the required grain size <0.8 mm. The weighing indicated approx. 500 g.

Chemical analysis of the solid matter; 51.5% $MgSO_4$; 27.1% urea; 21.4% water.

The content of magnesium sulfate and anhydrous magnesium sulfate was 0 wt. %.

The computational content of free urea was 1.5 wt. %.

The theoretical composition of the pure connection $MgSO4.CO(NH_2)_2\ 3\ H_2O$ is 51.3% $MgSO_4$, 25.6% urea and 23.1% water, or 11.9% N, 17.2% MgO and 13.7% S.

Example 2

562.8 g magnesium sulfate and 137.2 g granulated urea were mixed for 24 hours at 50° C. A fluid suspension was formed, into which a further 28 g of urea was then added. Then it was stirred for a further 24 hours at 50° C. After cooling to 30° C., the solid matter was filtered out and the drained, comminuted filter cakes were dried for 10 minutes at 40° C. in the laboratory fluidized bed. The yield of solid matter was 521 g.

Chemical analysis of the dried solid matter: 49.1% $MgSO_4$; 27.8% urea; 23.1% water.

The content of magnesium sulfate and anhydrous magnesium sulfate was 0 wt. %. The computational content at free urea was 2.2 wt. %.

Example 3

137.6 g anhydrous magnesium sulfate and 120.1 g granulated urea and 211.2 g magnesium sulfate were mixed well and warmed up to 50° C. Within 1 hour the consistence changed. The mixture first became moist and clotted.

With occasional agitation, a porridge formed which increasingly solidified. After cooling to room temperature, the mixture was hard and was comminuted. The weighing indicated approx. 469 g.

Chemical analysis of the solid matter: 54.0% $MgSO_4$; 26.5% urea; 19.5% water. The content of magnesium sulfate and anhydrous magnesium sulfate was 2.7 wt. %. The content of free urea was 0.9 wt. %.

The invention claimed is:

1. A composition comprising at least 80 wt %, based on a total weight of the composition, of a magnesium-sulfate-urea compound of Formula (I):

$$[MgSO_4 \cdot m\ CO(NH_2)_2 \cdot n\ H_2O] \qquad (I),$$

wherein
m is in a range from 0.9 to 1.1,
n is in a range from 2.9 to 3.1,
the composition comprises, based on the total weight of the composition, (i) less than 10 wt % of free $MgSO_4$ in an anhydrate form or in a form of a hydrate of the magnesium sulfate, (ii) less than 10 wt % uncombined urea, or both (i) and (ii), and
the composition is a solid material which is non-liquefying for at least 24 hours under ambient conditions.

2. The composition of claim 1, comprising, based on the total weight of the composition, (i) less than 5 wt % of free $MgSO_4$ in an anhydrate form or in a form of a hydrate of the magnesium sulfate, (ii) less than 5 wt % uncombined urea, or both (i) and (ii).

3. The composition of claim 1, wherein m in Formula (I) is 1.0.

4. The composition of claim 1, wherein in Formula (I) m is 1.0 and n is 3.0.

5. The composition of claim 1, comprising (i) less than 10 wt % of free $MgSO_4$ in an anhydrate form or in a form of a hydrate of the magnesium sulfate.

6. The composition of claim 1, comprising (ii) less than 10 wt % uncombined urea.

7. The composition of claim 1, comprising (i) less than 10 wt % of free $MgSO_4$ in an anhydrate form or in a form of a hydrate of the magnesium sulfate, and (ii) less than 10 wt % uncombined urea.

8. A fertilizer comprising the composition of claim 1.

9. A nitrogen-magnesium-sulfur fertilizer composition, comprising the composition of claim 1 and magnesium sulfate.

10. A nitrogen-magnesium-sulfur fertilizer composition, comprising the composition of claim 1 and at least one further component selected from the group consisting of a urease inhibitor and a nitrification inhibitor.

11. A process for making the composition of claim 1, comprising:
converting a mixture of an anhydrous magnesium sulfate with urea and water to the composition,
stirring of said mixture during said converting,
wherein a reaction temperature during said converting is between 30 to 70° C.,
wherein the anhydrous magnesium sulfate, urea and water are present in a molar ratio of magnesium sulfate to urea in a range from 1:0.9 to 1:1.1 and a molar ratio of magnesium sulfate to water in a range from 1:2.9 to 1:3.1, and
wherein the anhydrous magnesium sulfate and the urea are first mixed and the water is added to the mixture of anhydrous magnesium sulfate and urea.

12. The process of claim 11, further comprising granulating a reaction mass of the conversion mixture during the conversion, or immediately after the conversion, when the reaction mass is still plastic.

13. A process for making the composition of claim 1, comprising first converting a magnesium sulfate mixture with urea in a molar ratio in a range of 1:0.9 to 1:1.1 to obtain a mixure, and then adding urea to the mixture; wherein
the magnesium sulfate is of the formula $MgSO_4.7H_2O$.

14. The process of claim 13, wherein 10 to 30 mole % of urea, based on the initially employed amount of urea is added.

15. A process for making the composition of claim 1, comprising converting a mixture of an anhydrous magnesium sulfate, urea and magnesium sulfate to the composition, wherein a molar ratio of anhydrous magnesium sulfate: urea is in a range from 1:1.65 to 1:1.85 and a molar ratio of anhydrous magnesium sulfate:magnesium sulfate is in a range from 1:0.65 to 1:0.85, and
the magnesium sulfate is of the formula $MgSO_4.7H_2O$.

16. A process for irrigation fertilizing an agricultural or gardening substrate, comprising contacting the substrate with water, the composition of claim 1, and optionally one or more additives, with substantially no surplus water.

* * * * *